US006977318B2

(12) United States Patent
Bridges (10) Patent No.: US 6,977,318 B2
(45) Date of Patent: Dec. 20, 2005

(54) PROPYLENE PRODUCTION

(75) Inventor: Robert S. Bridges, Friendswood, TX (US)

(73) Assignee: Equistar Chemicals, LP, Houston, TX (US)

( * ) Notice: Subject to any disclaimer, the term of this patent is extended or adjusted under 35 U.S.C. 154(b) by 37 days.

(21) Appl. No.: 10/838,579

(22) Filed: May 4, 2004

(65) Prior Publication Data

US 2005/0250969 A1 Nov. 10, 2005

(51) Int. Cl.[7] .......................... C07C 1/24; C07C 1/207; C07C 6/04
(52) U.S. Cl. ...................... 585/324; 585/643; 585/645; 585/646; 585/647
(58) Field of Search ............................... 585/324, 643, 585/645, 646, 647, 638, 639, 671

(56) References Cited

U.S. PATENT DOCUMENTS

| 3,351,635 | A | 11/1967 | Kollar ...................... 260/348.5 |
| 3,510,538 | A | 5/1970 | Rosenthal ................... 260/682 |
| 3,665,048 | A | 5/1972 | Grane et al. ................ 260/682 |
| 4,036,905 | A | 7/1977 | Kornfeld .................... 260/682 |
| 4,423,271 | A | 12/1983 | Obenaus et al. ............. 585/639 |
| 5,107,001 | A | 4/1992 | Gelb et al. .................. 549/529 |
| 5,276,212 | A | 1/1994 | Luebke et al. .............. 568/697 |
| 5,424,458 | A | 6/1995 | Sullivan et al. ............. 549/529 |
| 5,625,109 | A | 4/1997 | Gupta ........................ 585/639 |
| 6,111,160 | A | 8/2000 | Powers et al. .............. 585/671 |
| 6,323,384 | B1 | 11/2001 | Powers et al. .............. 585/671 |
| 6,518,474 | B1 | 2/2003 | Sanderson et al. .......... 585/639 |
| 6,743,958 | B2 * | 6/2004 | Commereuc et al. ....... 585/324 |

OTHER PUBLICATIONS

R. L. Banks, *Journal of Molecular Catalysis*, vol. 8, p. 269-276, 1980, ISSN 0304-5102.

Robert L. Banks, "Discovery and Development of Olefin Disproportionation (Metathesis)," American Chemical Society Symposium, Series, No. 222, Heterogeneous Catalysis: Selected American Histories, B.H. Davis and W. P. Hettinger, Jr., Editors, *American Chemical Society*, 1983, ISSN 0097-6156.

* cited by examiner

*Primary Examiner*—Thuan D Dang
(74) *Attorney, Agent, or Firm*—Roderick W. MacDonald

(57) ABSTRACT

A method for forming propylene wherein ethylene is employed as a primary feed material in a combination of steps comprising dehydration, skeletal isomerization, and metathesis to form a versatile product mix that can contain one or more of propylene, gasoline, MTBE, and propylene oxide.

15 Claims, 6 Drawing Sheets

Invention

Prior Art

PROPYLENE PRODUCTION

BACKGROUND OF THE INVENTION

1. Field of the Invention

This invention relates to a method of making propylene. More particularly, this invention relates to the production of propylene, with or without the formation of methyl tertiary butyl ether (MTBE).

2. Description of the Prior Art

From time to time there exists in the world geographical areas or regions (areas), where propylene availability is either non-existent or in limited supply. There can be large areas, for example, Europe at present, where propylene is available, but only in limited supply.

There are other areas in the world where natural gas (gas) is available, but there is no gas pipeline nearby which can be used to transport the gas to market in an economical manner. This type of gas is known as "stranded" or "remote" gas. Natural gas usually contains both ethane and propane, both of which can be separated from the gas in its remote location. This can be done, for example, when forming liquefied natural gas for transportation to market on a natural gas liquids transport ship. Ethane can be converted in known manner into ethylene by a process generally known as pyrolysis or thermal cracking. Ethane cracking to form ethylene is commonly practiced in remote areas and is quite often the low-cost supply of ethylene in the world. On the other hand, propane dehydrogenation to form propylene is expensive and usually the highest cost supply. Further, in remote areas propane has a high value of its own as a cooking and heating fuel. This also dictates against using propane as a feedstock to produce propylene in remote areas.

Thus, ethylene can be economically produced, given a natural gas supply, even in remote areas, while the same is not true for propylene. This invention, by virtue of its use of ethylene, and not propylene, as a feedstock is highly useful anywhere there is a source of natural gas no matter how remote the location of that source, or where excess ethylene is available, such as Europe or North America.

There are yet other areas in the world that either limit or prohibit the use of MTBE in automotive gasoline. In some areas, although there is currently a demand for MTBE, that demand is gradually being reduced for various reasons.

Propylene under supply and MTBE over supply at first may appear to be unrelated problems, but, as will be seen hereinafter, they can be related.

This invention provides a solution for both propylene and MTBE supply problems, whether they be over supply, under supply, or a combination thereof, and does so in a manner that utilizes ethylene as the primary feed. Thus, this invention is useful in remote areas that contain stranded gas as well as other areas of the world that are not remote and have an available ethylene supply and a limited propylene supply.

SUMMARY OF THE INVENTION

In accordance with this invention, there is provided a method for forming propylene, along with certain valuable by-products, using ethylene as the primary feedstock along with one or more of tertiary butyl alcohol, isobutane, and methanol as co-feeds.

Depending on the co-feed materials employed in this invention along with the ethylene primary feed, a versatile product mix can be achieved. In addition to propylene, this product mix can contain one or more of propylene oxide (PO), MTBE, and gasoline.

The foregoing is accomplished by this invention with a combination of dehydration, skeletal (reverse) isomerization, and metathesis (disproportionation) steps, with or without the use of an etherification step, all as explained in detail hereinafter.

DESCRIPTION OF THE DRAWINGS

FIG. 2 is one embodiment within this invention. This embodiment uses ethylene and TBA as primary feed materials, and produces propylene and gasoline as products of the process. This embodiment is useful for making propylene without the co-production of MTBE in areas where MTBE demand is declining or non-existent.

FIG. 3 is another embodiment within this invention. It uses ethylene and isobutane and oxygen as primary feed materials, and produces propylene, PO, and gasoline as products of the process. This embodiment is also useful for making propylene in areas where MTBE demand is low or non-existent, and there is PO demand.

FIG. 5 shows that this embodiment uses less than half the mols of ethylene feed when compared to the prior art FIG. 1 propylene feed mols used, which is at least one-third less on a pound basis. This embodiment also makes about half the MTBE product when compared to prior art FIG. 1, which is an advantage in areas where the MTBE market exists, but is declining. This embodiment is also advantageous in areas where there is PO and MTBE demand, but propylene is available or in low supply.

FIG. 6 is a subset of FIG. 5 wherein the MTBE unit is not fed directly from the skeletal isomerization unit, but rather operates on an isobutylene/n-butenes stream from the metathesis unit. This embodiment is balanced as to propylene, viz., there is no excess (net) propylene product and no makeup propylene requirement.

In the foregoing FIGS. 1 through 6, mol numbers are set forth at various locations on the Figure itself. The mol numbers thus set forth are, for sake of clarity and ease of understanding and comparison, idealized conversions, viz., there is not normally 100% selectivity in any of the processes shown.

FIGS. 2 through 6 demonstrate that this invention is useful in areas where propylene is not readily available, but ethylene is available or can be made available such as by the thermal cracking of ethane.

DETAILED DESCRIPTION OF THE INVENTION

This invention will, for the sake of clarity, be described as employing various specific feeds such as tertiary butyl alcohol (t-butyl alcohol or TBA) and other specific process streams such as isobutylene. However, the processes within this invention are broadly applicable to the use of any hydrocarbon stream containing those various specific feeds and/or specific process streams with which the desired results of this invention can be obtained.

Figure 1:
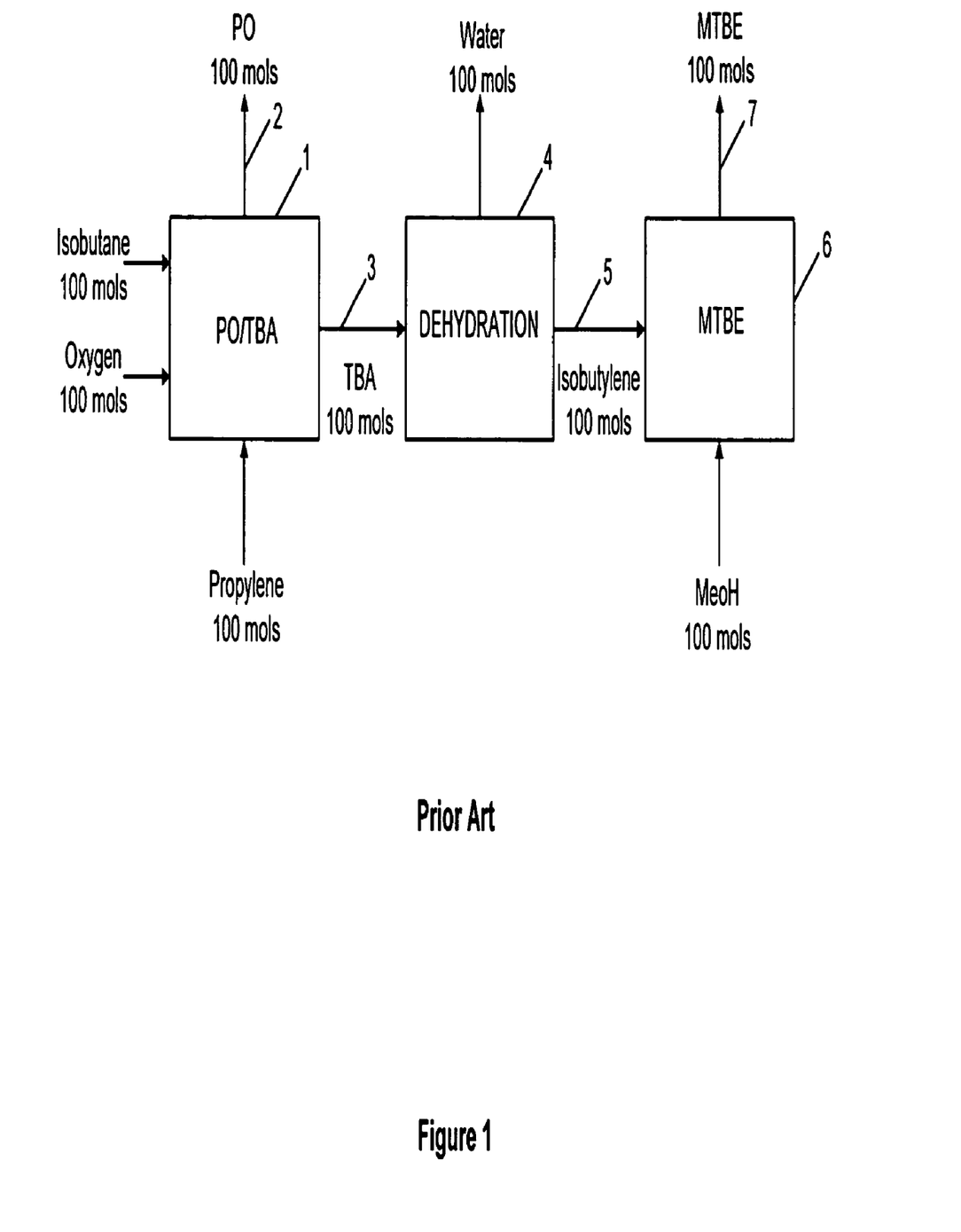
FIG. 1 shows a prior art process that is currently commercially practiced in both the United States and Europe. This process uses propylene as a primary feed, and produces significant amounts of PO and MTBE as products of the process.

FIG. 1 shows a conventional prior art process wherein isobutane and propylene are fed into a PO/TBA plant 1, propylene oxide product is removed from the process as a process product thereof at 2, and a product stream containing TBA produced in unit 1 is passed by way of line 3 to dehydration unit (zone or step) 4. In unit 4 the TBA in the product stream is dehydrated to form a water product and isobutylene which is passed as a product stream by way of line 5 to MTBE unit 6. Methanol is fed into unit 6 and therein reacted with isobutylene to form MTBE which is removed at 7 as another product of the process. This overall process, its various units, and its operating details are known in the art, see U.S. Pat. No. 5,107,001 (particularly units 4, 7, and 10) and U.S. Pat. No. 3,351,635. It can be seen from this Figure that this prior art process is a large consumer of propylene and a large producer of MTBE. In areas where there is little or no economic propylene supply and/or little or no MTBE demand, this process is at a disadvantage.

The prior art, represented by U.S. Pat. No. 5,107,001 above, has suggested a process wherein an n-butane forward skeletal isomerization unit is employed to form isobutane from n-butane. The isobutane is then used in an oxidation unit to form tertiary butyl hydroperoxide which is reacted with propylene in an epoxidation unit to make PO. The TBA formed in the PO/TBA plant is converted into separate ethylene, propylene, and MTBE products of the process. It can be seen that this prior art process consumes propylene in the epoxidation unit of the PO/TBA plant. Thus, this prior art produces no net propylene. Accordingly, no propylene is produced by this particular prior art process which could then be put to use in geographical areas where there is limited or no propylene supply. This prior art process is also a net producer of ethylene, not a consumer of ethylene like the present invention. Finally, this prior art process is a net producer of MTBE which is not a benefit in areas where MTBE demand is decreasing, already low, or non-existent.

Figure 2:
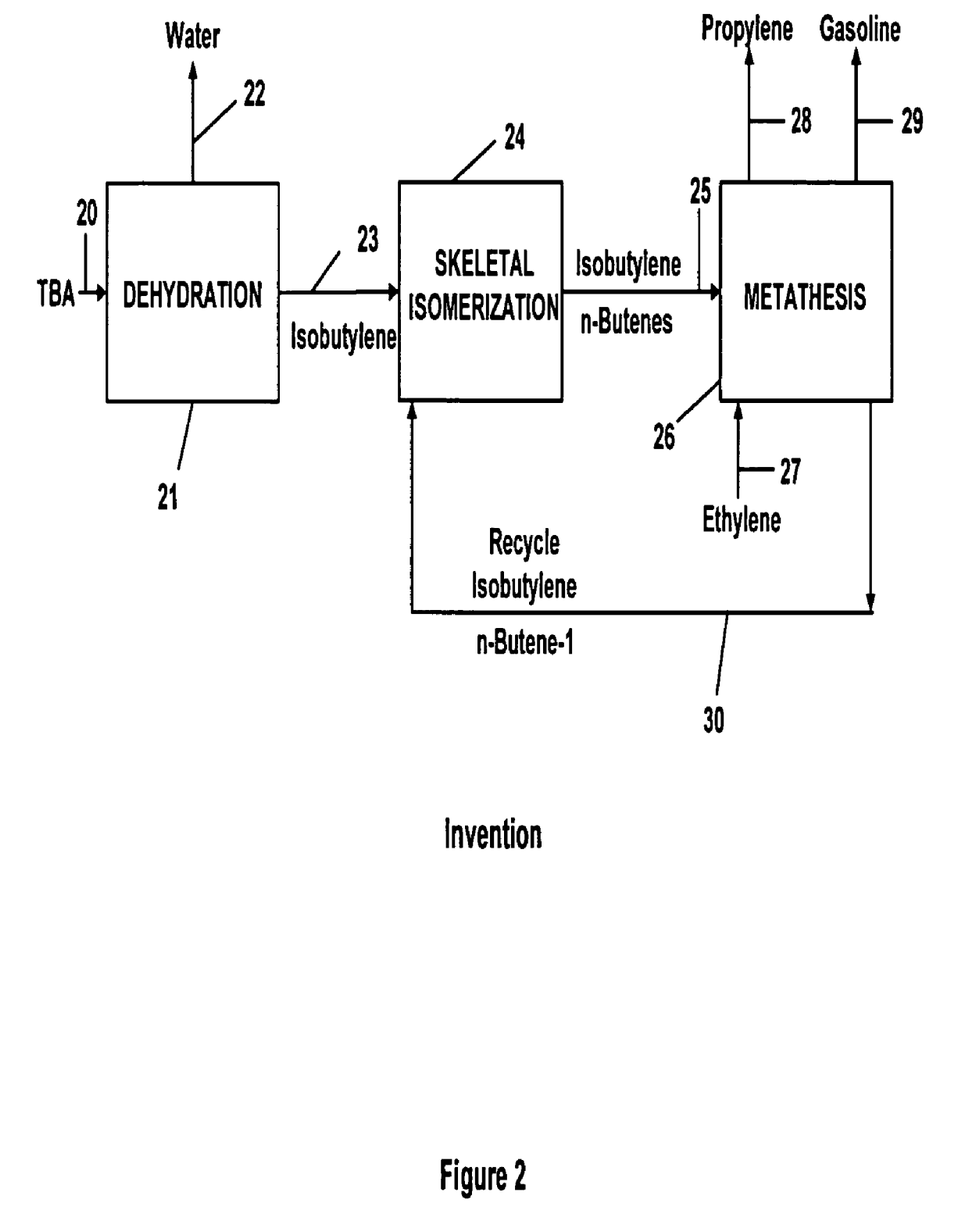

The present invention in one of its broadest aspects is represented by FIG. 2. This Figure shows TBA stream 20 as a primary feed to a dehydration unit 21. Unit 21 can be the same in operation as the dehydration unit of U.S. Pat. No. 5,107,001 (unit 13). In unit 21 TBA is dehydrated to form a water product 22 and an isobutylene product 23.

TBA dehydration is well known in the art, see U.S. Pat. Nos. 5,625,109; 4,036,905; 4,423,271; 3,510,538; and 6,518,474. Accordingly, operating conditions for this step of the process will vary widely within this invention, but are generally presently preferred to be a temperature of from about 475° F. to about 775° F. under a pressure of from about atmospheric to about 300 psig in the presence of an acidic catalyst. A wide variety of known acidic catalysts can be used, for example, alumina, alumino silicate, zeolite(s), clay(s), and acid treated clay(s), and the like; all of which, along with other known catalysts, are fully and completely disclosed in the patents cited above. Alumina is presently preferred, and can be a porous form of aluminum oxide of high surface area such as Alcoa's F-1 Activated Alumina, which is fully disclosed in U.S. Pat. No. 3,665,048.

Isobutylene 23 of FIG. 2 is passed to skeletal isomerization unit 24 wherein at least part of the isobutylene feed is converted to a mixture of n-butenes (butene-1 and butene-2). This isomerization step is known in the art, see U.S. Pat. Nos. 6,111,160 and 6,323,384. Generally, the operating conditions for this unit 24 will be a temperature of from about 450° F. to about 1200° F. a pressure of from about 0 to about 150 psig, and a weight hourly space velocity of from about 1.0 to about 50 h$^{-1}$. Skeletal isomerization catalysts useful in this invention are known in the art, and include zeolites having one-dimensional pore structures with a pore size ranging from greater than about 0.42 nanometers (nm) to less than about 0.7 nm.

The product of unit 24 is a mixture of isobutylene and n-butenes which is passed by way of line 25 to metathesis unit 26. In unit 26, butene-2 is disproportionated with ethylene from line 27 to form propylene 28 as a product of the process. Some of the butene-1 and butene-2 react together in unit 26 to form propylene and pentene-2. The pentene-2 along with other heavier molecules go into the formation of a separate gasoline co-product 29 composed of hydrocarbons boiling in the conventional gasoline boiling range of from about 100° F. to about 420° F. Unreacted isobutylene and butene-1 are recycled by way of line 30 to isomerization unit 24 wherein at least some of the recycle isobutylene is converted into a mixture of additional n-butenes for use in unit 26. In unit 24, butene-1 is isomerized in part to butene-2. Also, due to the low butene-2 content in recycle stream 30, additional butene-2 is formed by the recycle butene-1 converting on its own to its natural equilibrium mixture of butene-1 and butene-2. Further, as noted above, some butene-1 goes into the making of propylene and 2-pentene. Thus, isobutylene and butene-1 are recycled to extinction by way of stream 30.

Metathesis operating conditions can vary widely and are known in the art. Generally the conditions are a temperature of from about 300° F. to about 800° F., a pressure of from about 200 to about 600 psig, and a weight hourly space velocity of from about 1.0 to about 100 h$^{-1}$.

Suitable catalysts that promote, preferably primarily promote, metathesis as described herein are known in the art, and include at least one of halides, oxides, and/or carbonyls of at least one of molybdenum, tungsten, rhenium, and/or magnesium carried on a support such as silica and the like. The conversion of butene-2 in the presence of excess ethylene to propylene is known; see R. L. Banks, Journal of Molecular Catalysis, Vol. 8, pp. 269–276, 1980, ISSN 0304-5102. For more information on olefin metathesis, see Discovery and Development of Olefin Disproportionation (Metathesis) by Robert L. Banks, American Chemical Society Symposium Series No. 222, Heterogeneous Catalysis: Selected American Histories, B. H. Davis and W. P. Hettinger, Jr., Editors, American Chemical Society, 1983, ISSN 0097-6156.

This invention can use, but is not limited to, TBA from a PO/TBA plant, for example, the plants described in FIG. 1 above and the prior art patents cited above. This is shown in FIG. 3.

Figure 3:
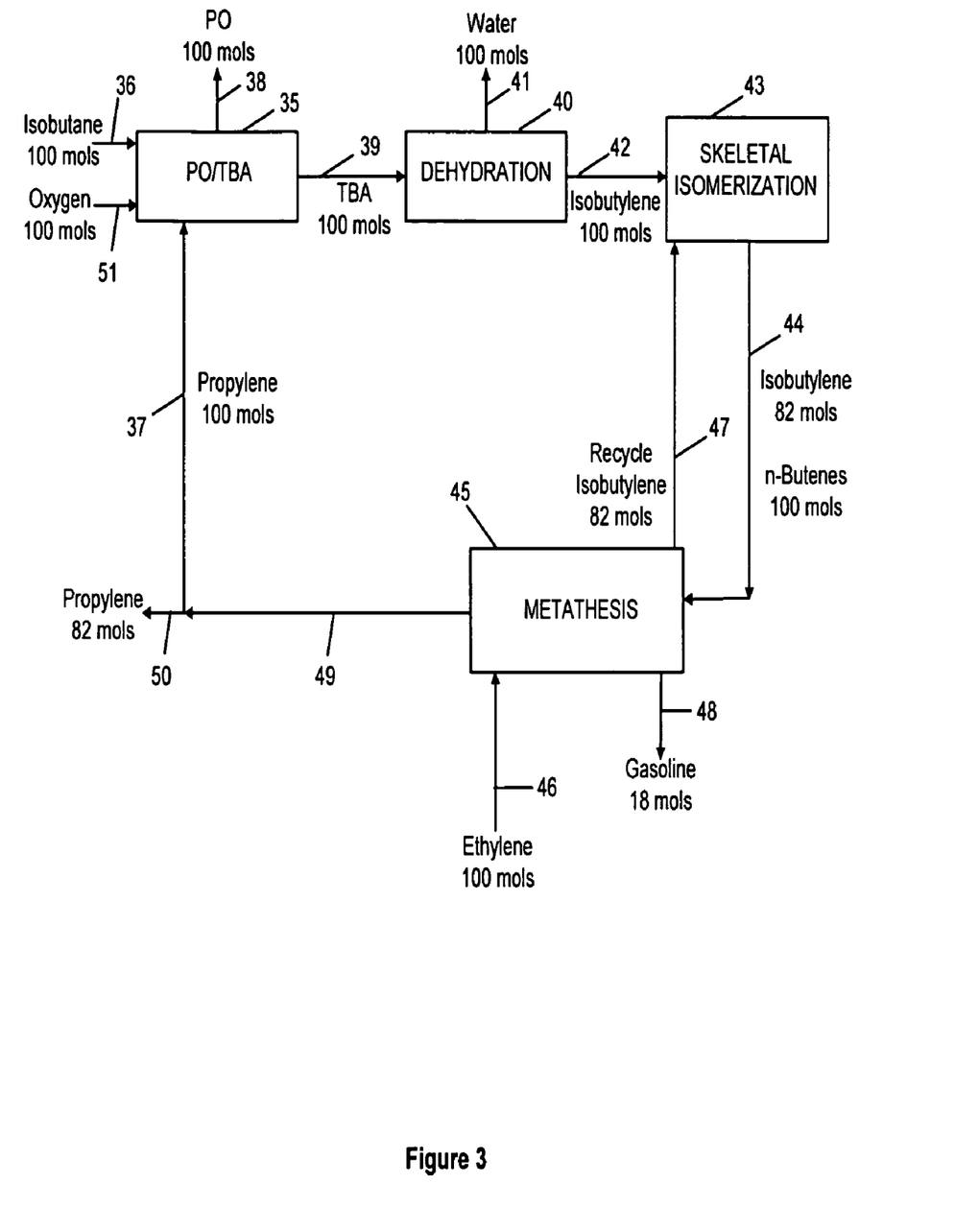

In FIG. 3, a conventional PO/TBA plant 35 is employed. Unit 35 can be the same as that described here in above in respect of unit 1 of FIG. 1. Unit 35 operates on isobutane feed 36, oxygen feed 51, and propylene feed 37 to form a PO product 38 and a separate TBA product 39. In accordance with this invention, TBA is dehydrated in unit 40 to form water 41 and isobutylene 42. Unit 40 can be the same type unit described for units 4 and 21 of FIGS. 1 and 2 above. Isobutylene 42 is passed to skeletal isomerization unit 43 wherein at least part of the isobutylene 42 is converted to a mixture of n-butenes as described above. Unit 43 can be the same as that described for unit 24 of FIG. 2 above. A mixture of isobutylene and n-butenes is passed by way of line 44 to metathesis zone 45 wherein butene-2 is metathesized with an ethylene primary feed 46 to form propylene 49 and a gasoline by-product 48 as described above with reference to unit 26 of FIG. 2. Unit 45 can be the same as unit 26 of FIG. 2. A stream 47 containing isobutylene is recycled from unit 45 to unit 43 wherein at least some of the recycled isobutylene is converted to additional n-butenes. Propylene as a product of the process is removed from unit 45 by way of line 49. Propylene product 49 can be passed, at least in part, by way of line 37 for use as feed for unit 35. Net propylene product can be removed from the process by way of line 50.

The embodiment of FIG. 3, in effect, uses ethylene to form PO with a net production of propylene and no production of MTBE, a unique combination of feeds and products. This is quite useful in areas where both PO and propylene are in demand, but MTBE is not.

Figure 4:
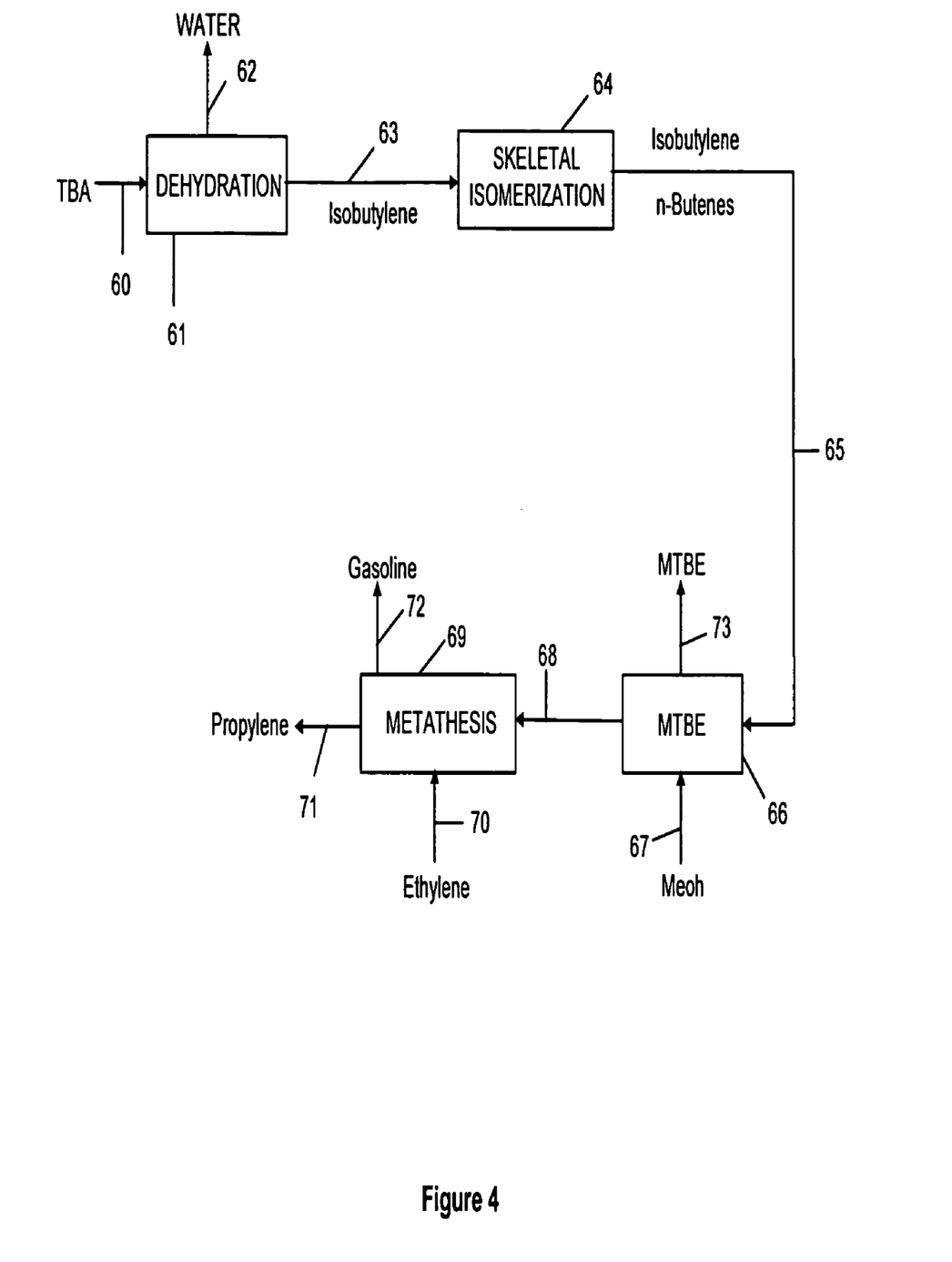
FIG. 4 is yet another embodiment within this invention which uses ethylene, TBA, and methanol as primary feed materials, and produces propylene, MTBE, and gasoline as products of the process. This embodiment can be used for making propylene in areas where there is MTBE demand.

FIG. 4 shows an embodiment wherein TBA 60 is used as a primary feed to a dehydration unit 61 from which is produced water 62 and isobutylene 63. Unit 61 can be the same as units 4, 21, and 40 of FIGS. 1–3 above. Isobutylene 63 is passed to skeletal isomerization unit 64 wherein at least some of the isobutylene is converted to a mixture 65 of isobutylene and n-butenes, as described above. Unit 64 can be the same as units 24 and 43 of FIGS. 2 and 3 above. In this embodiment, instead of passing stream 65 directly to a metathesis unit as shown in FIG. 3, stream 65 is instead passed into an MTBE producing unit 66 wherein part of the isobutylene in stream 65 is reacted with methanol from stream 67 to form MTBE as a product of the process. A mixture of n-butenes and any remaining, unreacted isobutylene is removed from unit 66 and passed by way of line 68 to a metathesis unit 69 wherein at least some of the butene-2 from line 68 is metathesized with feed ethylene 70 to form propylene 71 and gasoline 72 as products of the process. Unit 69 can be the same as units 26 and 45 of FIGS. 2 and 3. In this embodiment there need not be recycle of isobutylene from unit 69 to unit 64, contrary to that shown in FIG. 3 above.

FIG. 4 shows the versatility of this invention, in that it can produce the desired propylene product in areas where propylene is in limited supply, and at the same time produce MTBE when there is also MTBE demand in those areas.

The operating conditions for forming MTBE are known; see U.S. Pat. Nos. 5,276,212 and 5,424,458. The operating conditions for an MTBE unit can vary widely, but will generally be a temperature of from about 85° F. to 210° F., a pressure of from about 140 to about 580 psig, and a methanol to isobutylene weight ratio of from about 1/1 to about 2/1 using any of the known etherification catalysts. Such catalysts include mineral acid such as sulfuric acid, boron trifluoride, phosphoric acid on kieselguhr, phosphorus modified zeolites, heteropoly acids, and sulfonated resins, all as fully and completely disclosed in the above U.S. patents.

Figure 5:
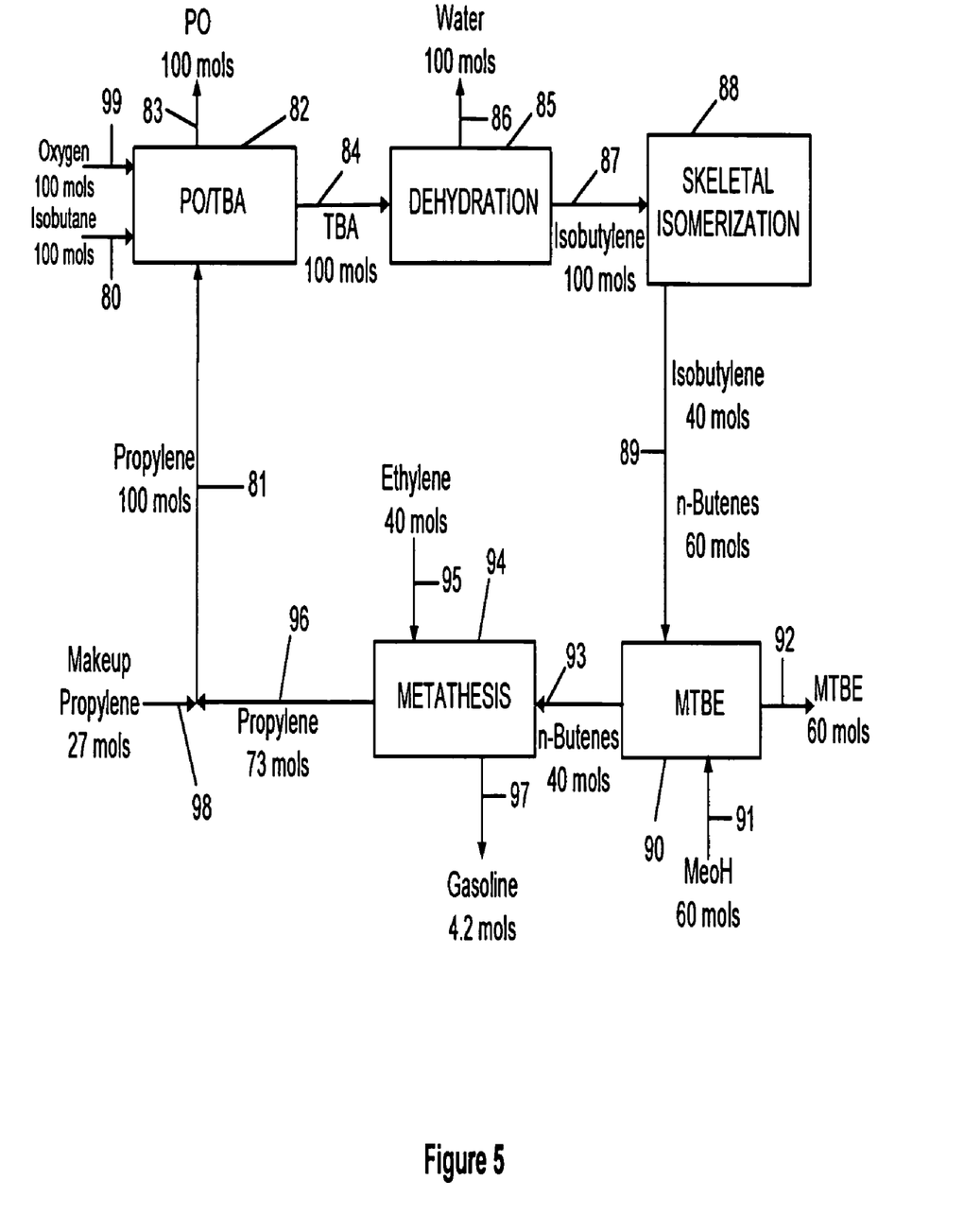
FIG. 5 is a further embodiment within this invention which uses ethylene, isobutane, oxygen, and methanol as primary feed materials, and produces propylene for use in a PO plant, MTBE, and gasoline. This embodiment utilizes at least part of its propylene product to form PO in areas where PO is in demand, but propylene supply is limited or not available.

If desired, the MTBE producing aspect of this invention can be coupled with a PO/TBA plant as described in FIG. 3 above. In this case at least some of the propylene product can be used to advantage in the formation of PO when there is PO demand. FIG. 5 shows this embodiment wherein isobutane feed 80, oxygen feed 99, and propylene feed 81 are passed into a PO/TBA plant 82. PO stream 83 is formed as a product of the process, while TBA product stream 84 is passed to dehydration unit 85. Unit 85 can be the same as units 4, 21, 40, and 61 of FIGS. 1–4. Water 86 and an isobutylene containing product stream 87 are formed by unit 85. Stream 87 is passed to isomerization unit 88 wherein a mixture of n-butenes is formed from at least part of the isobutylene in stream 87. Unit 88 can be the same as units 24, 43, and 64 of FIGS. 2–4. A mixture of isobutylene and n-butenes 89 is passed to MTBE unit 90 wherein isobutylene is reacted with methanol 91 to form MTBE 92 as a product of the process. Unit 90 can be the same as units 6 and 66 of FIGS. 1 and 4. A mixture of n-butenes 93 is separated from unit 90 and passed to unit 94 wherein butene-2 is metathesized with ethylene from feed stream 95 to produce, as process products, of propylene stream 96 and gasoline stream 97. Recycle of isobutylene from unit 94 to unit 88 is not required. Propylene product can be passed by way of lines 96 and 81 to PO/TBA plant 82 as feed therefore. Makeup propylene is added to the process by way of line 98.

The embodiment of FIG. 5 is useful where there is demand for PO and MTBE, but propylene is in limited supply.

Figure 6:
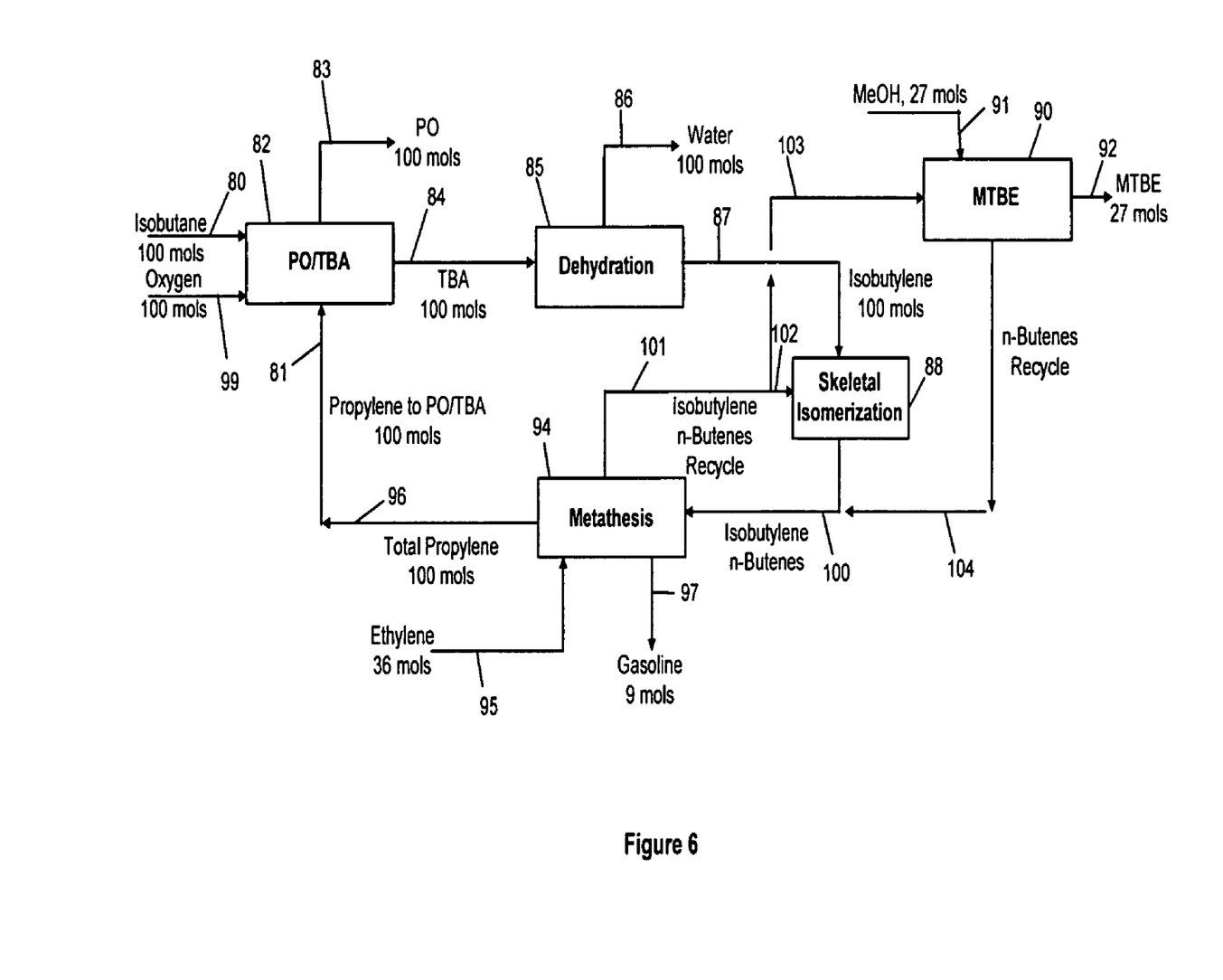
FIG. 6 is another embodiment within this invention.

FIG. 6 shows a propylene balanced embodiment in which all the propylene needed for the process is generated within the process so that there is no net propylene produced by the process, but at the same time there is no need for makeup propylene to be added to the process. FIG. 6 shows the use of PO/TBA unit 82, dehydration unit 85, skeletal isomerization unit 88, MTBE unit 90, and metathesis unit 94 all as described for FIG. 5 here in above.

The difference between FIGS. 5 and 6 is that in FIG. 6 the output of skeletal isomerization unit 88 passes directly to metathesis unit 94 by way of line 100 instead of, as shown in FIG. 5, to MTBE unit 90 by way of line 89.

In addition, in FIG. 6 an isobutylene/n-butenes stream 101 is removed from metathesis zone 94 and passed to at least one of isomerization zone 88 by way of line 102 or MTBE zone 90 by way of lines 102 and 103. The split between lines 102 and 103 is adjusted so as to help maintain the balanced propylene mode aforesaid. A recycle stream 104 of n-butenes can be removed from unit 90 and returned as feed to unit 94 by way of line 100. This also helps maintain the balanced propylene mode.

FIGS. 2–6 above can each employ ethylene derived from stranded natural gas by thermally cracking ethane removed from that gas. They can also employ ethylene from other supplies of ethane or ethylene not related to stranded gas.

EXAMPLE

Tertiary-butyl alcohol is fed into a dehydration zone, unit 21 of FIG. 2, wherein it is dehydrated in the liquid phase to primarily isobutylene and water at 600° F. and 200 psig using alumina as a catalyst. The catalyst is present in a concentration of about 2.5 weight percent (wt %) based on the total weight of the liquid reaction mixture. A vaporous reaction mixture is removed from the unit which mixture, after cooling to about 90° F. at 20 psia and removal of liquid condensation products, yields a final isobutylene product stream that contains about 96.4 wt % isobutylene, about 1.1 wt % water, about 1.1 wt % TBA, and about 1.4 wt % isobutanol.

The final isobutylene product stream is fed to a skeletal isomerization zone, unit 24 of FIG. 2, wherein a substantial amount of the branched chain isobutylene in the isobutylene product stream is converted into a mixture of linear butene-1 and butene-2 using a temperature of about 700° F. under a pressure of about 16 psig at a weight hourly space velocity of about 5 $h^{-1}$, and a zeolite catalyst having one-dimensional pores of about 0.50 nm. In this isomerization step, on a single pass basis, there is about a 40 wt % conversion of isobutylene with an 80 percent selectivity to butene-1 and butene-2. The product stream containing isobutylene, butene-1, and butene-2 is fed to a metathesis zone, unit 26 of FIG. 2.

In the metathesis zone, butene-2 is disproportionated with a molar excess of ethylene to form propylene and a gasoline by-product using a catalyst composed of a mixture of tungsten oxide and magnesium oxide at a temperature of about 625° F. and pressure of about 400 psig. A stream containing propylene is separated from this zone as a product of the process, while a separate stream containing essentially hydrocarbons boiling in the gasoline boiling range of from about 100° F. to about 420° F. is also removed as a product of the process. A third stream is removed which contains isobutylene and butene-1, but is depleted in butene-2, and recycled to the isomerization unit 24 for the generation of additional amounts of butene-2 which are then made available for disproportionation in unit 26 and the formation of yet additional amounts of propylene. Isobutylene and butene-1 are recycled from unit 26 to unit 24 to extinction.

Reasonable variations and modifications are possible within the scope of this disclosure without departing from the spirit and scope of this invention.

I claim:

1. A method for forming propylene comprising providing a feed containing at least in part t-butyl alcohol, subjecting said feed to dehydration conditions which favor the conversion of said t-butyl alcohol to isobutylene to form a first stream that contains isobutylene at least in part, subjecting said first stream to skeletal isomerization conditions wherein at least part of said isobutylene is converted to a mixture of butene-1 and butene-2 to form a second stream that contains at least in part isobutylene, butene-1 and butene-2, subjecting said second stream to disproportionation with an ethylene feed under conditions that favor the metathesis of at least part of said butene-2 present in said second stream with said ethylene feed to form propylene and a gasoline by-product, recycling a stream from said metathesis step to said isomerization step, said recycle stream containing at least in part isobutylene and butene-1 so that in said skeletal isomerization step at least part of said recycled isobutylene is converted to additional butene-1 and butene-2 and at least part of said recycled butene-1 is converted to a mixture of butene-1 and butene-2, and recovering from said metathesis step a propylene stream as a product of the process and a separate gasoline stream as a by-product of the process.

2. The method of claim 1 wherein the source of said t-butyl alcohol feed is a propylene oxide/t-butyl alcohol plant that reacts propylene with isobutane and oxygen to form separate products comprising propylene oxide and t-butyl alcohol, at least a portion of said propylene product stream from said metathesis step is employed as feed to said plant, and the remainder of said propylene product stream is removed from the process as a product thereof.

3. The method of claim 1 wherein said second stream is passed as feed to a methyl tertiary butyl ether formation process wherein at least part of the isobutylene present in said second stream is reacted with methanol to form methyl tertiary butyl ether as a product of the process, separating from said methyl tertiary butyl ether formation step a third stream containing at least in part butene-1 and butene-2, and passing said third stream to said disproportionation step to metathesize at least part of the butene-2 in said third stream with ethylene to form said propylene product of the process.

4. The method of claim 3 wherein there is no recycle stream from said metathesis step to said skeletal isomerization step.

5. The method of claim 1 wherein the source of said t-butyl alcohol feed is a propylene oxide/t-butyl alcohol plant that reacts propylene with isobutane and oxygen to form separate products comprising propylene oxide and t-butyl alcohol, said second stream is passed to a methyl tertiary butyl ether step wherein at least part of the isobutylene present in said second stream is reacted with methanol to form methyl tertiary butyl ether as a product of the process, separating from said methyl tertiary butyl ether formation step a third stream containing at least in part butene-1 and butene-2, passing said third stream to said disproportionation step to metathesize at least part of the butene-2 in said third stream with ethylene to form said propylene product, passing at least part of said propylene product as feed to said plant.

6. The method of claim 5 wherein there is no recycle stream from said metathesis step to said skeletal isomerization step.

7. The method of claim 1 wherein said skeletal isomerization step operating conditions are a temperature of from about 450° F. to about 1,200° F., a pressure of from about 0 to about 150 psig, and a weight hourly space velocity of from about 1 to about 50 $h^{-1}$.

8. The method of claim 7 wherein said skeletal isomerization step employs a catalyst comprising at least one zeolite having one dimensional pore structures with a pore size ranging from greater than about 0.42 nm to less than about 0.7 nm.

9. The method of claim 1 wherein said metathesis step operating conditions are a temperature of from about 300° F. to about 800° F., a pressure of from about 200 to about 600 psig, and a weight hourly space velocity of from about 1 to about 100 $h^{-1}$.

10. The method of claim 9 wherein said metathesis step employs a supported catalyst consisting essentially of at least one of halides, oxides, and carbonyls of at least one of molybdenum, tungsten, rhenium, and magnesium.

11. The method of claim 1 wherein said dehydration operating conditions are a temperature of from about 475° F. to about 775° F., a pressure of from about atmospheric to about 300 psig, and an acidic catalyst.

12. The method of claim 11 wherein said catalyst is at least one material selected from the group consisting essentially of alumina, alumino silicate, zeolite, clay, and acid treated clay.

13. The method of claim 5 wherein said methyl tertiary butyl ether formation step operating conditions are a temperature of from about 85° F. to about 210° F., a pressure of from about 140 to about 580 psig, a methanol to isobutylene weight ration of from about 1/1 to about 2/1, and an etherification promoting catalyst.

14. The method of claim 13 wherein said catalyst is selected from the group consisting essentially of mineral acid, zeolite, heteropoly acid, and sulfonated resins.

15. The method of claim 1 wherein the source of said t-butyl alcohol feed is a propylene oxide/t-butyl alcohol plant that reacts propylene with isobutane and oxygen to form separate products comprising propylene oxide and t-butyl alcohol, said second stream is passed to said disproportionation step to metathesize at least part of the butene-2 with ethylene to form propylene, passing said propylene as feed to said propylene oxide/t-butyl alcohol plant, separating from said metathesis unit a stream containing isobutylene and n-butenes and passing at least part of said stream as feed to said methyl tertiary butyl ether formation step, recovering from said methyl tertiary butyl ether step a stream containing n-butenes and returning said stream as feed to said disproportionation step.

* * * * *